(12) United States Patent
Li et al.

(10) Patent No.: US 10,408,728 B2
(45) Date of Patent: Sep. 10, 2019

(54) EXPERIMENTAL DEVICE AND METHOD FOR STUDYING RELATIONSHIP BETWEEN SEDIMENT YIELD BEHAVIOR AND RADIAL DEFORMATION OF POROUS MEDIA DURING EXPLOITATION OF NATURAL GAS HYDRATES

(71) Applicant: GUANGZHOU INSTITUTE OF ENERGY CONVERSION, CHINESE ACADEMY OF SCIENCES, Guangzhou (CN)

(72) Inventors: Xiaosen Li, Guangzhou (CN); Yi Wang, Guangzhou (CN); Ningsheng Huang, Guangzhou (CN); Gang Li, Guangzhou (CN); Yu Zhang, Guangzhou (CN); Zhaoyang Chen, Guangzhou (CN)

(73) Assignee: Guangzhou Institute of Energy Conversion, Chinese Academy of Sciences, Guangzhou (CN)

( * ) Notice: Subject to any disclaimer, the term of this patent is extended or adjusted under 35 U.S.C. 154(b) by 228 days.

(21) Appl. No.: 15/497,183

(22) Filed: Apr. 25, 2017

(65) Prior Publication Data
US 2018/0172574 A1    Jun. 21, 2018

(30) Foreign Application Priority Data
Dec. 20, 2016 (CN) .......................... 2016 1 1186227

(51) Int. Cl.
| | |
|---|---|
| *G01N 15/04* | (2006.01) |
| *G01B 21/32* | (2006.01) |
| *B01J 3/04* | (2006.01) |
| *B01J 3/03* | (2006.01) |
| *E21B 49/00* | (2006.01) |

(52) U.S. Cl.
CPC .............. *G01N 15/04* (2013.01); *B01J 3/03* (2013.01); *G01B 21/32* (2013.01);
(Continued)

(58) Field of Classification Search
CPC ............. B01L 2208/00955; B01L 2219/00011
(Continued)

(56) References Cited

U.S. PATENT DOCUMENTS

| | | | | |
|---|---|---|---|---|
| 5,226,310 A | * | 7/1993 | Steiger ................... | E21B 49/006 73/38 |
| 5,243,855 A | * | 9/1993 | Steiger ................... | E21B 49/006 73/152.52 |

(Continued)

OTHER PUBLICATIONS

Kimoto, S., et al., "A chemo—thermo—mechanically coupled analysis of ground deformation induced by gas hydrate dissociation", International Journal of Mechanical Sciences, 2010, 52, pp. 365-376.

(Continued)

*Primary Examiner* — Daniel S Larkin
(74) *Attorney, Agent, or Firm* — Harvest IP Law LLP

(57) ABSTRACT

Disclosed is an experimental device for studying the sediment yield behavior and the radial deformation of porous media during the exploitation of natural gas hydrates, comprising a high-pressure reactor, a hydrate sample chamber, a simulated wellbore, a deformation measurement unit, an ambient temperature control unit, an outlet control unit, an inlet control unit and a data processing unit. Further disclosed is a method using the above-mentioned experimental device to carry out experiments. The experimental device and method according to the present invention can conveniently measure the deformation of the porous media during the decomposition of the hydrates and simulate the sediment producing situation in the wellbore, can simulate the sediment yield problem during the exploitation of natural gas hydrates as well as the gas-liquid-solid flowing problem in the wellbore during the exploitation of natural gas hydrates, and can accurately obtain the gas-solid-liquid three-phase yields in real time during the decomposition of natural gas (Continued)

hydrates. Being simple to operate and easy to control, and suitable for various sizes and shapes of reactors, it can provide basic experimental data and a theoretical basis for the technologies of hydrate exploitation.

7 Claims, 3 Drawing Sheets

(52) U.S. Cl.
CPC ............... *B01J 2208/00955* (2013.01); *B01J 2219/00011* (2013.01); *E21B 49/00* (2013.01)

(58) Field of Classification Search
USPC ...................................................... 73/118.01
See application file for complete search history.

(56) References Cited

U.S. PATENT DOCUMENTS

| | | | | |
|---|---|---|---|---|
| 5,275,063 A * | 1/1994 | Steiger | ................ | G01N 33/241 73/865.6 |
| 5,325,723 A * | 7/1994 | Meadows | ................ | G01N 3/10 100/106 |
| 6,055,874 A * | 5/2000 | Onan | ...................... | E21B 49/00 73/865.6 |
| 7,089,816 B2 * | 8/2006 | Hakimuddin | ............ | G01N 3/00 73/865.6 |
| 9,841,531 B2 * | 12/2017 | Li | ............................ | E21B 43/00 |
| 2016/0251943 A1 * | 9/2016 | Li | ............................ | B01J 12/02 422/162 |
| 2016/0305205 A1 * | 10/2016 | Li | .......................... | E21B 47/00 |

OTHER PUBLICATIONS

Hyodo, M. et al., "Effects of dissociation on the shear strength and deformation behavior of methane hydrate-bearing sediments", Marine and Petroleum Geology, 2014, 51, pp. 52-62.

Han, H. et al., "Experimental study on sediment deformation during methane hydrate decomposition in sandy and silty clay sediments with a novel experimental apparatus", Fuel, 2016, 182, pp. 446-453.

* cited by examiner

EXPERIMENTAL DEVICE AND METHOD FOR STUDYING RELATIONSHIP BETWEEN SEDIMENT YIELD BEHAVIOR AND RADIAL DEFORMATION OF POROUS MEDIA DURING EXPLOITATION OF NATURAL GAS HYDRATES

CROSS REFERENCE TO RELATED APPLICATION

This application claims priority benefits from Chinese Patent Application CN 201611186227.5, filed on Dec. 20, 2016 at the State Intellectual Property Office of the People's Republic of China.

FIELD OF THE INVENTION

The present invention relates to the field of exploiting natural gas hydrates, and more specifically, to an experimental device and a method for studying the relationship between the sediment yield behavior and the radial deformation of porous media during the exploitation of natural gas hydrates.

BACKGROUND OF THE INVENTION

Natural gas hydrates (NGH) are a kind of cage-like crystalline compound formed from natural gas and water under a low temperature and high pressure. With a snow and ice-like appearance, NGHs, commonly known as "combustible ice", will burn immediately in case of a fire. The natural gas in the natural gas hydrates found in nature is mainly composed of methane (>90%). Under the normal temperature and pressure, 1 m$^3$ of natural gas hydrate decomposes and releases about 160 m$^3$ of natural gas, so natural gas hydrates have an extremely high energy density. The natural gas hydrates found in nature mainly exists in the sediments of the continental shelf of the oceans and the continental tundra. In 1964, scientists discovered natural gas hydrates in the Siberian tundra for the first time, and soon also discovered natural gas hydrates in the seabed sediments in the Black Sea. By the 1990s, scholars in the industry agreed that the energy stored in the global natural gas hydrates exceeded the total energies stored in all oil, coal and natural gas. Over the past 20 years, a plurality of programs including deep sea drilling programs (DSDP), the ocean drilling programs (ODP) and integrated ocean drilling programs (IODP) have been launched worldwide to investigate the mineral resources of natural gas hydrates. At present, the total volume of the global natural gas hydrates is estimated to be about 1015~1018 standard cubic meters. Therefore, natural gas hydrates are considered as the energy source with the most potential for replacing oil and natural gas in the 21st century. A survey on resources shows that China's South China Sea, the continental slope of the East China Sea—Okinawa, and the tundra of the Qinghai-Tibet Plateau are all reserves of natural gas hydrates. Therefore, carrying out studies on the effective, rapid and economical method for exploiting natural gas hydrates to provide an experimental basis and evidence for large-scale exploitation of natural gas hydrates is an effective way to alleviate the increasing pressure on energies.

The exploitation technology for natural gas hydrates is one of the key links to realize the development and utilization of natural gas hydrate resources. Unlike conventional fossil fuels, natural gas hydrates are present in porous media in solid form. The basic idea of the exploitation is to change the temperature—pressure environments, or the phase equilibrium conditions of the hydrates, under which natural gas hydrates can exist stably so as to make the solid hydrates in the reservoir in situ decompose into natural gas and water, and then the natural gas can be exploited. Accordingly, scientists have proposed several conventional exploiting technologies, such as the pressure reduction method, the heat stimulation method and the chemical reagent method. Due to the complicated geological environment and the diversified forms of the mineral reserves of the hydrates, as well as the complicated phase change process and multi-phase seepage process of the multi-phase system composed of the natural gas-water-sediment-hydrate-ice, the change of the skeleton of the porous media accompanying the hydrate decomposition during the exploitation of hydrates is one of the largest problems encountered during the exploitation of hydrates currently. The original geological characteristics of the mineral reserves of the hydrates will change greatly (for example, the permeability, the porosity, the mechanical properties and the pore pressure will all change drastically), as natural gas hydrates reserved in solid form change into flowing water and gas, thus resulting in the deformation of the porous media and the gas-solid-liquid three-phase mixed flow field, which may eventually lead to ground deformation. Therefore, carrying out studies on the influence of the sediment yield behavior on the deformation of porous media in the decomposition of natural gas hydrates plays an important role in the successful completion of the hydrate production technology and the safety thereof.

Currently, the studies on the relatively advanced exploitation of natural gas hydrates around the world are focused on the effect of different exploiting methods for the phase-change decomposition of the hydrates and the consuming transfer of the heat in the decomposition of the hydrates. For a real condition, the understanding of the complicated mechanism of the phase-change seepage in the decomposition of the hydrates is still in a vague state. In almost all simulated experiments of hydrate exploitation, the relationship between sediment yield behavior and the deformation of porous media during the exploitation of hydrates has been neglected. In the prior simulated experiments, the porous media (particle diameter >100 µm) composed of large particles were used to make the skeleton of the porous media unchangeable during the decomposition of the hydrates, but the porous media with actual particle diameters in the mineral reserves of the hydrates are composed of particles with sizes ranging from 0.01 µm (micro-particles) to 500 µm (large particles) together, and sediment yield behavior and deformation are unavoidable during the exploitation of hydrates. Particularly, the radial deformation of the porous media around the well may be the main factor resulting in the collapsing of the well wall and sediment yield behavior. At present, there are no effective experimental methods for measuring the radial deformation caused by hydrate decomposition. Currently, the experimental devices of natural gas hydrates exploitation are becoming more accurate and are developing in line with the actual modes of the outdoors; however, the implementation of specific projects is still faced with great challenges. The research achievements of the existing laboratory devices cannot fully meet the needs for technologies providing safe and economic field exploitation of the hydrates, and there is a need for further research and development of advanced experimental equipment and platforms which enable a more accurate inversion of the actual changes during the exploitation of hydrate reserves in the seabed and the operating situations of the exploiting equipment so as to lay a solid foundation for the realization of safe and reliable exploitation.

SUMMARY OF THE INVENTION

In view of the above-mentioned shortcomings in the prior art, one of the objectives of the present invention is to provide an experimental device for studying the relationship between the sediment yield behavior and the radial deformation of porous media during the exploitation of natural gas hydrates. By the provision of a real-size exploiting wellbore and a removable perforating adapter, the sediment yield behavior and the gas-liquid-solid flowing behavior in the wellbore during the exploitation of hydrates can be simulated for obtaining the data of the sediment yield behavior and the radial deformation of porous media during hydrate exploitation so as to discover the relationship between the sediment yield behavior and the deformation of porous media, thus providing the basic experimental data and the theoretical basis for the technologies of hydrate exploitation.

To achieve the objective above, the present invention adopts the following technical solution:

an experimental device for studying the relationship between sediment yield behavior and the radial deformation of porous media during the exploitation of natural gas hydrates, comprising a high-pressure reactor, a hydrate sample chamber, a simulated wellbore, a deformation measurement unit, an ambient temperature control unit, an outlet control unit, an inlet control unit and a data processing unit;

the high-pressure reactor provided in the ambient temperature control unit and used for providing a confining pressure that simulates an actual geological condition, comprising an upper cap of the reactor, a body of the reactor and a lower cap of the reactor;

the high-pressure reactor is further provided with a flexible rubber sleeve which forms the hydrate sample chamber with the upper cap and the lower cap of the reactor, wherein the hydrate sample chamber is filled with porous media with a particle diameter of less than 100 μm, and the flexible rubber sleeve, the body of the reactor, the upper of the reactor and lower caps of the reactor form a confining pressure chamber;

the simulated wellbore is a hollow cylindrical structure with its side wall provided with a perforation is located in the hydrate sample chamber and used for simulating the sediment yield behavior during the exploitation of hydrates;

the deformation measurement unit comprises a set of radial deformation measurement units including a plurality of hard connecting rods radially and evenly distributed along the flexible rubber sleeve, wherein one end of the hard connecting rod is connected with the outer wall of the flexible rubber sleeve, and the other end penetrates the outer wall of the body of the high-pressure reactor and is connected with a displacement sensor which is used for measuring the movement of the hard connecting rods to obtain the radial deformation of porous media in the hydrate sample chamber;

the ambient temperature control unit is used for controlling the temperature during the processes of the generation, decomposition and sampling of the hydrate in the high-pressure reactor;

the inlet control unit is used for injecting water and natural gas into the hydrate sample chamber;

the outlet control unit is used for controlling the pressure of the outlet of the simulated wellbore during the exploitation of hydrates and conducting separation of the products at the outlet and data measurement;

the sensing elements of the high-pressure reactor, the deformation measurement unit, the ambient temperature control unit, the outlet control unit and the inlet control unit are all electrically connected with the data processing unit through signal lines, wherein the data processing unit is used for collecting and processing the sensing signals of all sensing elements.

The outlet control unit comprises a liquid-solid separator, an outlet pressure controller and a gas-liquid separator which are sequentially communicated, wherein the liquid-solid separator is provided at the outlet of the simulated wellbore.

A plurality of sets of radial deformation measurement units provided and evenly distributed along the axial direction of the flexible rubber sleeve are used for measuring the radial deformation of the porous media in the axial direction.

The size of the simulated wellbore is equal to that of the actual drilling wellbore, and the perforation of the simulated wellbore is further provided with an adapter which is used for changing the size of the perforation and removably provided on the perforation.

The adapter is further provided with a sediment control net used for simulating the sediment control and/or a dead plug for simulating a blocked state.

The simulated wellbore is further provided with a sensor and an endoscope used for directly measuring and observing the sediment yield condition and the flowing condition in the wellbore.

The upper and lower caps and the body of the high-pressure reactor all adopt a clamp fixing structure, and the rubber ring sealing enables the high-pressure reactor to provide the maximum confining pressure of up to 25 Mpa.

Another objective of the present invention is to provide an experimental method for studying the relationship between the sediment yield behavior and the radial deformation of porous media during the exploitation of gas hydrates, so that the sediment yield behavior and the gas-liquid-solid flowing behavior in the wellbore during the exploitation of hydrates can be simulated for obtaining the data of the sediment yield behavior and the radial deformation of porous media in the hydrate exploitation so as to find out the relationship between the sediment yield behavior and the deformation of porous media, thus providing the basic experimental data and the theoretical basis for the technologies of the hydrate exploitation. The experimental method comprises the following steps:

S1. placing the high-pressure reactor in the ambient temperature control unit, placing the simulated wellbore in the hydrate sample chamber, and filling the porous media with a particle diameter of less than 100 μm in the hydrate sample chamber;

S2. setting the experimental ambient temperature, setting the experimental confining pressure of the high-pressure reactor, and injecting the water and the natural gas into the hydrate sample chamber through the inlet control unit to generate a gas hydrate sample;

S3. when the generation of natural gas hydrates is completed, keeping the confining pressure of the high-pressure reactor constant and controlling the decomposition temperature through the ambient temperature control unit to conduct the decomposition of the gas hydrate sample;

S4. controlling the outlet pressure of the simulated wellbore through the outlet control unit and measuring the yields of the gas, the water and the sediments in the simulated wellbore in real time through the outlet control unit;

S5. measuring the deformation of the porous media in the hydrate sample chamber through the deformation measurement unit;

S6. analyzing and calculating the deformation of the porous media and the yields of the gas, the water and the sediments in the simulated wellbore to obtain the relationship between the sediment yield behavior and the radial deformation of porous media during the exploitation of gas hydrates.

The step of controlling the outlet pressure of the simulated wellbore through the outlet control unit further comprises the following steps: firstly, filling the liquid-solid separator of the outlet control unit with the water and keeping the pressure in the liquid-solid separator the same with that in the high-pressure reactor, and then opening the outlet valve of the simulated wellbore to control the outlet pressure of the simulated wellbore through the outlet pressure control valve.

The step of measuring the yields of the gas, the water and the sediments in the simulated wellbore in real time through the outlet control unit further comprises the following steps: firstly, separating the sediments through the liquid-solid separator, weighing the changes of the weight of a screen desander in the liquid-solid separator and measuring the yields of the sediments in real time, and then measuring the yields of the water in real time through an electronic balance and measuring the yields of the gas in real time through a gas flow meter after the liquid that has flowed out from the liquid-solid separator is further separated into the water and the gas through the gas-liquid separator.

Compared with those in the prior art, the beneficial effects of the present invention are as below:

1. By the provision of a set of the radial deformation measurement units on the flexible rubber sleeve, the radial deformation of the porous media in a circumferential section thereof can be measured, and by the provision of a plurality of sets of the radial deformation measurement units along the axial direction of the flexible rubber sleeve, the radial deformation of the porous media in several circumferential sections from top to bottom thereof can be measured, so that the overall condition of the radial deformation of the porous media can be obtained; the measuring method using the hard connecting rod in combination with the flexible rubber sleeve overcomes the shortcoming that the radial deformation of the porous media cannot be measured in the high-pressure reactor; compared with the conventional measurement method which can only measure the axial deformation through the movement of an axial piston rod, the present invention can accurately measure the radial deformation of the porous media during the exploitation of natural gas hydrates and the measuring method using the flexible sleeve connected with the hard connecting rod will not impact the deformation of the porous media and the process of the sediment yield behavior, so it has the advantages of a simple structure and a good effect of measurement.

2. The yields of the gas, the water and the sediments can be measured in real time through the outlet control unit, and an analysis on the yields of the gas, the water and the sediments as well as the radial deformation of the porous media can be conducted through the data processing unit so as to find out the relationship between them, thus providing the basic experimental data and the theoretical basis for the technologies of the hydrate exploitation.

3. The provision of the real-size simulated wellbore with its size equal to that of an actual wellbore can more truly simulate the possible sediment yield problem occurring during the exploitation of natural gas hydrates, the provision of the adapter which can adjust the size of the perforation can realize different tests without the replacement of the simulated wellbore, and the provision of the sediment control net or the dead plug on the adapter can more truly simulate the gas-liquid-solid flowing problem in the wellbore during the exploitation of natural gas hydrates.

4. By the provision of the sensor and the endoscope in the simulated wellbore, the sediment yield condition and the flowing condition in the wellbore can be directly measured and observed.

Figure 2:
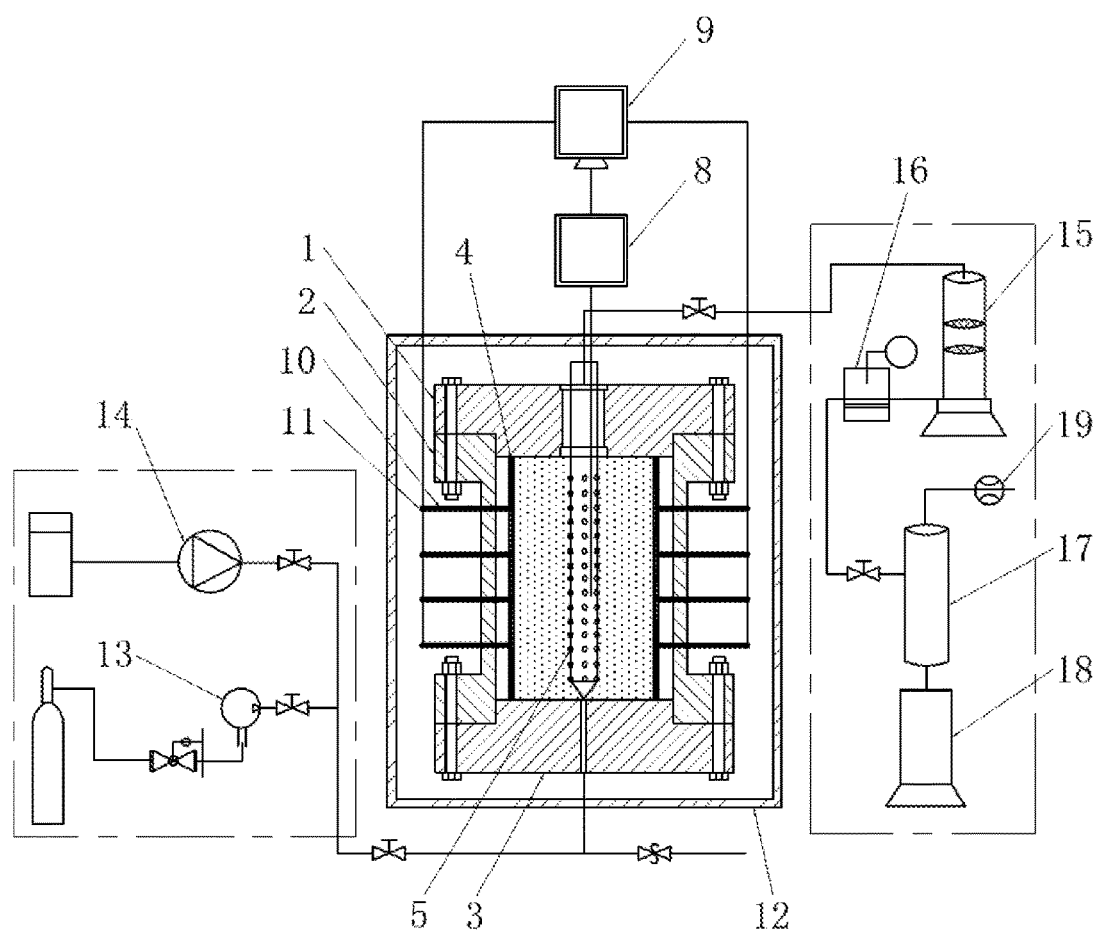
FIG. 2 is a structural diagram of the experimental device of the present invention.
Figure 3:
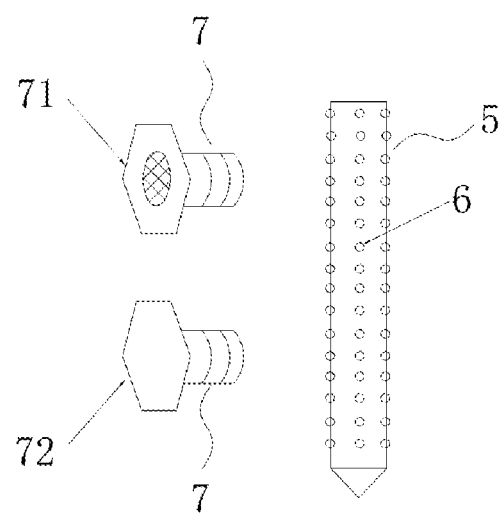
FIG. 3 is a detailed view of a simulated wellbore with perforation, an adapter with a sediment control net, and an adapter with a dead plug.

Reference numbers for FIGS. 2 and 3: 1: upper cap of the reactor; 2: body of the reactor; 3: lower cap of the reactor; 4: flexible rubber sleeve; 5: simulated wellbore; 6: perforation; 7: adapter; 71: sediment control net; 72: dead plug; 8: display screen of endoscope; 9: data processing unit; 10: hard connecting rod; 11: displacement sensor; 12: thermostatic water-bath; 13: booster pump; 14: constant-flux pump; 15: liquid-solid separator; 16: outlet pressure controller; 17: gas-liquid separator; 18: electronic balance; 19: gas flow meter.

DETAILED DESCRIPTION OF THE EMBODIMENTS

The present invention is further detailed in combination with the drawings and embodiments as below.

Embodiment

Figure 1:
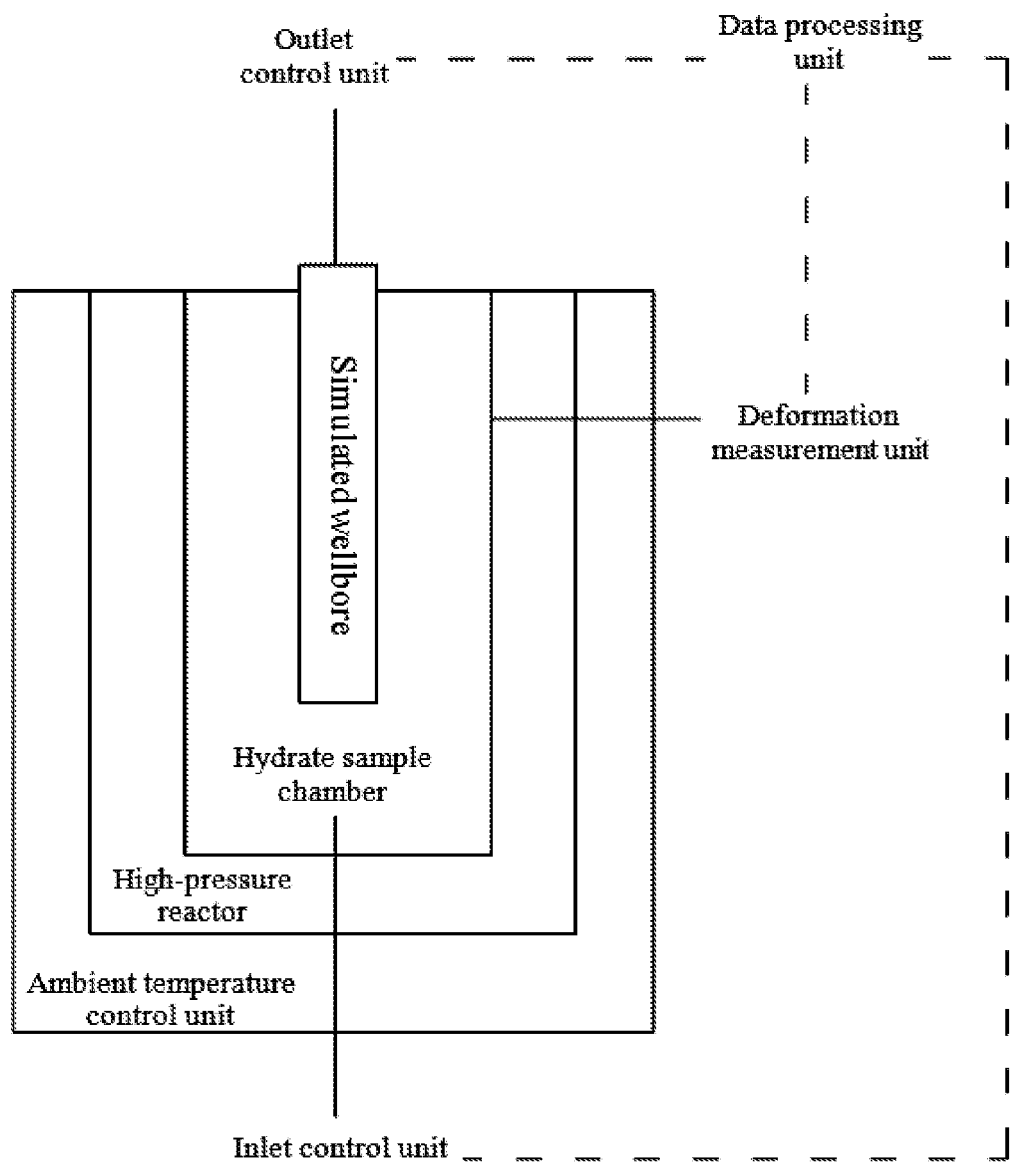
FIG. 1 is a block diagram of the experimental device of the present invention.

As shown in FIG. 1 and FIG. 2, an experimental device for studying the relationship between the sediment yield behavior and the radial deformation of porous media during the exploitation of natural gas hydrate comprises a high-pressure reactor, a hydrate sample chamber, a simulated wellbore 5, a deformation measurement unit, an ambient temperature control unit, an outlet control unit, an inlet control unit and a data processing unit 9.

The high-pressure reactor provided in the ambient temperature control unit and used for providing a confining pressure that simulates an actual geological condition comprises an upper cap of the reactor 1, a body of the reactor 2 and a lower cap of the reactor 3; the upper cap of the reactor 1 and the lower cap of the reactor 3 and the body of the reactor 2 can adopt a bolt fixing mode, as shown in FIG. 2, or a clamp fixing structure through the rubber ring sealing which enables the high-pressure reactor to provide the maximum confining pressure of up to 25 Mpa.

The high-pressure reactor is further provided with a flexible rubber sleeve 4 which forms the hydrate sample chamber with the upper cap of the reactor 1 and the lower cap of the reactor 3, wherein the hydrate sample chamber is filled with porous media with a particle diameter of less than 100 µm, the hydrate is generated in the porous media, and the flexible rubber sleeve 4, the body of the reactor 2, the upper cap of the reactor 1 and the lower cap of the reactor 3 form a confining pressure chamber; in this embodiment, the hydrate sample chamber is cylindrical, and the internally-filled porous medium is preferably an actual sediment sample. In the prior simulated experiments, the porous media composed of large particles (particle diameter >100 μm) cannot change the skeleton of the porous media in the decomposition of the hydrates, while the particle diameter of the porous media in the present invention is less than 100 μm, so that the change of the skeleton of the porous media caused by the decomposition of the hydrate can be visually observed.

As shown in FIG. 2 and FIG. 3, the simulated wellbore 5 is a hollow cylindrical structure with its side wall provided with a perforation 6 is located in the hydrate sample chamber and used for simulating the sediment yield behavior during the exploitation of hydrates; the size of the simulated wellbore 5 is equal to that of an actual drilling wellbore, which can more truly simulate the possible sediment yield problem occurring during the exploitation of natural gas hydrates. The perforation 6 of the simulated wellbore 5 is further provided with an adapter 7 which is used for changing the size of the perforation 6 and removably provided on the perforation 6; the adapter 7 is further provided on one end outside the simulated wellbore 5 with a sediment control net 71 used for simulating the sediment control and/or a dead plug 72 for simulating a blocked state so as to investigate the sediment producing and controlling means of the hydrates; the simulated wellbore 5 is further provided with a sensor connected with the data processing unit 9 and an endoscope connected with the data processing unit 9 through the display screen of endoscope 8 which are used for directly measuring and observing the sediment yield condition and the flowing condition in the wellbore 5.

The deformation measurement unit comprises at least a set of radial deformation measurement units comprising a plurality of hard connecting rods 10 radially and evenly distributed along the flexible rubber sleeve 4, wherein the hard connecting rods 10 are made of stainless steel, one end of the hard connecting rod 10 is connected with the outer wall of the flexible rubber sleeve 4, and the other end penetrates the outer wall of the body of the reactor 2 of the high-pressure reactor and is connected with a displacement sensor 11 which is electrically connected with the data processing unit 9 and used for measuring the movement of the hard connecting rods 10 to obtain the radial deformation of porous media in the hydrate sample chamber;

The radial deformation measurement unit can measure the radial deformation of one circumferential section of the flexible rubber sleeve 4; the radial deformation measurement unit in the present embodiment comprises two sets of hard connecting rods 10 and a displacement sensor 11 respectively provided on the left and right sides of the flexible rubber sleeve 4; it is certain that four or more sets can be provided for the purpose of a higher accuracy of the measurement. To measure the radial deformation of the porous media in the entire flexible rubber sleeve 4, the present embodiment is sequentially provided with four sets of radial deformation measurement units from top to bottom along the axial direction of the flexible rubber sleeve 4 so as to accurately measure the hydrate sample chamber of the overall deformation of the porous media.

The ambient temperature control unit adopting a thermostatic water-bath 12 is used for controlling the temperature during the processes of the generation, decomposition and sampling of the hydrate in the high-pressure reactor.

The inlet control unit injects a predetermined amount of natural gas into the hydrate sample chamber through a booster pump 13, and injects a predetermined amount of water into the hydrate sample chamber through a constant-flux pump 14.

The outlet control unit which is connected at the outlet of the simulated wellbore 5 and used for controlling the outlet pressure of the simulated wellbore 5 during the exploitation of hydrates and conducting the separation of the products at the outlet and the data measurement of gas-liquid-solid, comprises a liquid-solid separator 15, an outlet pressure controller 16 and a gas-liquid separator 17 which are sequentially communicated, wherein the liquid-solid separator 15 is provided at the outlet of the simulated wellbore 5; the purpose of this design is to prevent the sediments produced in the simulated wellbore 5 from blocking the outlet pressure controller 16 which will result in an uncontrolled outlet pressure, and to prevent the fluid separator 15 from impacting the internal pressure of the high-pressure reactor; the liquid-solid separator 15 needs to be filled with water before the experiment so as to keep the pressure consistent with the internal pressure of the high-pressure reactor, then the liquid-solid separator 15 and the high-pressure reactor is communicated, and then the outlet valve of the simulated wellbore is opened, so that the outlet pressure of the simulated wellbore 5 can be controlled through the outlet pressure control valve 16.

For the products from the simulated wellbore 5: firstly, the sediments are separated through the liquid-solid separator 15, the changed weights of a screen desander in the liquid-solid separator 15 are weighted for measuring the yields of the sediments in real time, and then the yields of the water are measured in real time through an electronic balance 18 and the yields of the gas are measured in real time through a gas flow meter 19 after the liquid that has flowed out from the liquid-solid separator 15 is further separated into the water and the gas through the gas-liquid separator 17.

The sensing elements of the high-pressure reactor, the deformation measurement unit, the ambient temperature control unit, the outlet control unit and the inlet control unit are all electrically connected with the data processing unit 9 through signal lines, wherein the data processing unit 9 is used for collecting and processing the sensing signals of all sensing elements.

The experimental method using the above-mentioned experimental device for studying the sediment yield behavior and the radial deformation of porous media during the exploitation of natural gas hydrates in the embodiment of the present invention comprises the following steps:

S1. placing the high-pressure reactor in the ambient temperature control unit, placing the simulated wellbore 5 in the hydrate sample chamber, and filling the porous media with a particle diameter of less than 100 μm in the hydrate sample chamber;

S2. setting the experimental ambient temperature, setting the experimental confining pressure of the high-pressure reactor, and injecting the water and the natural gas into the hydrate sample chamber through the inlet control unit to generate a gas hydrate sample;

S3. when the generation of natural gas hydrates is completed, keeping the confining pressure of the high-pressure reactor constant and controlling the decomposition temperature through the ambient temperature control unit to conduct the decomposition of the gas hydrate sample;

S4. controlling the outlet pressure of the simulated wellbore 5 through the outlet control unit and measuring the yields of the gas, the water and the sediments in the simulated wellbore 5 in real time through the outlet control unit;

S5. measuring the deformation of the porous media in the hydrate sample chamber through the deformation measurement unit;

S6. analyzing and calculating the deformation of the porous media and the yields of the gas, the water and the sediments in the simulated wellbore to obtain the relationship between the sediment yield behavior and the deformation of porous media during the exploitation of gas hydrates.

The step of controlling the outlet pressure of the simulated wellbore 5 through the outlet control unit further comprises the following steps: firstly, filling the liquid-solid separator 15 of the outlet control unit with the water and keeping the pressure in the liquid-solid separator 15 the same as that in the high-pressure reactor, and then opening the outlet valve of the simulated wellbore 5 to control the outlet pressure of the simulated wellbore 5 through the outlet pressure control valve 16.

The step of measuring the yields of the gas, the water and the sediments in real time through the outlet control unit further comprises the following steps: firstly, separating the sediments through the liquid-solid separator 15, weighing the changes of the weight of a screen desander in the liquid-solid separator 15 and measuring the yields of the sediments in real time, and then measuring the yields of the water in real time through an electronic balance 18 and measure the yields of the gas in real time through a gas flow meter 19 after the liquid that has flowed out from the liquid-solid separator 15 is further separated into the water and the gas through the gas-liquid separator 17.

Compared with the existing experimental device, the experimental device for studying the relationship between the sediment yield behavior and the radial deformation of porous media during the exploitation of natural gas hydrates disclosed in the present invention has the following obvious advantages:

(1) By the provision of a set of the radial deformation measurement units on the flexible rubber sleeve, the radial deformation of the porous media in a circumferential section thereof can be measured, and by the provision of a plurality of sets of the radial deformation measurement units along the axial direction of the flexible rubber sleeve, the radial deformation of the porous media in several circumferential sections from top to bottom thereof can be measured, so that the overall condition of the radial deformation of the porous media can be obtained; the measuring method using the hard connecting rod in combination with the flexible rubber sleeve can accurately measure the radial deformation of the porous media during the exploitation of natural gas hydrates, so it has the advantages of a simple structure and a good effect of measurement.

(2) The yields of the gas, the water and the sediments can be measured in real time through the outlet control unit, and an analysis on the yields of the gas, the water and the sediments, as well as the radial deformation of the porous media can be conducted through the data processing unit so as to find out the relationship between them, thus providing the basic experimental data and the theoretical basis for the technologies of the hydrate exploitation.

(3) The provision of the real-size simulated wellbore with its size equal to that of an actual wellbore can more truly simulate the possible sediment yield problem occurring during the exploitation of natural gas hydrates, the provision of the adapter which can adjust the size of the perforation can realize different tests without the replacement of the simulated wellbore, and the provision of the sediment control net or the dead plug on the adapter can more truly simulate the gas-liquid-solid flowing problem in the wellbore during the exploitation of natural gas hydrates.

(4) By the provision of the sensor and the endoscope in the simulated wellbore, the sediment producing condition and the flowing condition in the wellbore can be directly measured and observed.

The embodiments mentioned above are only briefed to describe the technical concept and the characteristics of the present invention in order to make those skilled in this art capable of understanding the contents of the invention and implement it based on the contents, but not intended to limit the protection scope of the present invention. Any equivalent modifications or amendments made based on the essence of the contents of the present invention shall all be included in the protection scope of the present invention.

The invention claimed is:

1. An experimental device for studying the relationship between a sediment yield behavior and a radial deformation of porous media during an exploitation of natural gas hydrates, comprising: a reactor, a hydrate sample chamber, a simulated wellbore, a deformation measurement unit, an ambient temperature control unit, an outlet control unit, an inlet control unit and a data processing unit; wherein the reactor provided in the ambient temperature control unit configured for providing a confining pressure that simulates an actual geological condition comprises an upper cap of the reactor, a body of the reactor and a lower cap of the reactor;

the reactor is further provided with a flexible rubber sleeve which forms the hydrate sample chamber with the upper cap of the reactor and the lower cap of the reactor, wherein the hydrate sample chamber is filled with porous media with a particle diameter of less than 100 μm, and the flexible rubber sleeve, the body of the reactor, the upper and lower caps of the reactor form a confining pressure chamber;

the simulated wellbore comprises a hollow cylindrical structure with its side wall provided with a perforation is located in the hydrate sample chamber configured for simulating the sediment yield behavior during the exploitation of hydrates;

the deformation measurement unit comprises a set of radial deformation measurement units including a plurality of connecting rods radially and evenly distributed along the flexible rubber sleeve, wherein one end of each of the plurality of connecting rods is connected with an outer wall of the flexible rubber sleeve, and the other end penetrates an outer wall of the body of the reactor and is connected with a displacement sensor which is configured for measuring the movement of the connecting rods to obtain the radial deformation of porous media in the hydrate sample chamber;

the ambient temperature control unit is configured for controlling the temperature during the processes of a generation, decomposition and sampling of the hydrate in the reactor;

the inlet control unit is configured for injecting water and natural gas into the hydrate sample chamber;

the outlet control unit is configured for controlling the pressure of an outlet of the simulated wellbore during the exploitation of hydrates and conducting a separation of products at the outlet and a data measurement; and a sensing elements of the reactor, the deformation measurement unit, the ambient temperature control unit, the outlet control unit and the inlet control unit are all electrically connected with the data processing unit through signal lines, wherein the data processing unit is configured for collecting and processing the sensing signals of all sensing elements.

2. The experimental device according to claim 1, wherein the outlet control unit further comprises a liquid-solid separator, an outlet pressure controller and a gas-liquid separator which are sequentially communicated, wherein the liquid-solid separator is provided at the outlet of the simulated wellbore.

3. The experimental device according to claim 2, wherein a plurality of sets of the radial deformation measurement units provided and evenly distributed along the axial direction of the flexible rubber sleeve are used for measuring the radial deformation of the porous media in the axial direction.

4. The experimental device according to claim 3, wherein the size of the simulated wellbore is equal to that of the actual drilling wellbore, and the perforation of the simulated wellbore is further provided with an adapter which is used for changing the size of the perforation and removably provided on the perforation.

5. The experimental device according to claim 4, wherein the adapter is further provided with a sediment control net used for simulating the sediment control and/or a dead plug for simulating a blocked state.

6. The experimental device according to any one of claims 1-5, wherein the simulated wellbore is further provided with a sensor and an endoscope used for directly measuring and observing the sediment producing condition and the flowing condition in the wellbore.

7. The experimental device according to claim 6, wherein the upper of the reactor and lower cap of the reactor and the body of the reactor of the reactor all adopt a clamp fixing structure, and the rubber ring sealing enables the reactor to provide the maximum confining pressure of up to 25 Mpa.

* * * * *